United States Patent [19]

Ivri et al.

[11] Patent Number: 5,586,550
[45] Date of Patent: *Dec. 24, 1996

[54] APPARATUS AND METHODS FOR THE DELIVERY OF THERAPEUTIC LIQUIDS TO THE RESPIRATORY SYSTEM

[75] Inventors: Yehuda Ivri, Irvine; Cheng H. Wu, Sunnyvale, both of Calif.

[73] Assignee: Fluid Propulsion Technologies, Inc., Santa Clara, Calif.

[*] Notice: The term of this patent shall not extend beyond the expiration date of Pat. No. 5,164,740.

[21] Appl. No.: 521,641

[22] Filed: Aug. 31, 1995

[51] Int. Cl.$^6$ .............................. A61M 11/00
[52] U.S. Cl. .................. 128/200.16; 128/200.14; 239/406
[58] Field of Search ............ 239/4, 102.2, 110, 239/120, 121, 122; 347/47, 54, 20, 68; 222/196; 128/200.14, 200.16, 203.21, 203.12

[56] References Cited

U.S. PATENT DOCUMENTS

| | | | |
|---|---|---|---|
| 3,812,854 | 5/1974 | Michaels et al. | 128/200.16 |
| 4,119,096 | 10/1978 | Drews | 128/200.16 |
| 4,159,803 | 7/1979 | Cameto et al. | 239/102 |
| 4,268,460 | 5/1981 | Boiarski et al. | 261/1 |
| 4,300,546 | 11/1981 | Kruber | 128/200.16 |
| 4,301,093 | 11/1981 | Eck | 261/1 |
| 4,334,531 | 6/1982 | Reichl et al. | 128/200.14 |
| 4,338,576 | 7/1982 | Takahashi et al. | 331/67 |
| 4,465,234 | 8/1984 | Maehara et al. | 239/102 |
| 4,533,082 | 8/1985 | Maehara et al. | 239/102 |
| 4,632,311 | 12/1986 | Nakane et al. | 239/101 |
| 4,790,479 | 12/1988 | Matsumoto et al. | 239/102.2 |
| 4,793,339 | 12/1988 | Matsumoto et al. | 239/102.2 |
| 4,850,543 | 7/1989 | Takahashi et al. | 128/200.16 |
| 4,887,989 | 10/1989 | Drews et al. | 310/323 |
| 4,976,259 | 12/1990 | Higson et al. | 128/200.18 |
| 5,063,922 | 11/1991 | Häkkinen | 128/200.16 |
| 5,076,266 | 12/1991 | Babaev | 128/200.16 |
| 5,139,016 | 8/1992 | Waser | 128/200.16 |
| 5,152,456 | 10/1992 | Ross et al. | 239/102.2 |
| 5,164,740 | 11/1992 | Ivri | 346/1.1 |
| 5,170,782 | 12/1992 | Kocinski | 128/200.16 |
| 5,261,601 | 11/1993 | Ross et al. | 239/102.2 |
| 5,487,378 | 1/1996 | Robertson et al. | 128/200.16 |

FOREIGN PATENT DOCUMENTS

| | | | |
|---|---|---|---|
| 0178925 | 4/1986 | European Pat. Off. | 128/200.16 |
| 477885 | 10/1969 | Switzerland | 128/200.16 |
| 2101500 | 1/1983 | United Kingdom . | |

OTHER PUBLICATIONS

D. C. Cipolla et al., "Assessment of Aerosol Delivery Systems for Recombinant Human Deoxyribonuclease," *S.T.P. Pharma Sciences* 4 (1) 50–62, 1994.

D. C. Cipolla et al., "Characterization of Aerosols of Human Recombinaint Deoxyribonuclease I (rhDNase) Generated by Jet Nebulizers," *Pharmaceutical Research* 11 (4) 491–498, 1994.

I. Gonda, "Therapeutic Aerosols," *Pharmaceutics, The Sci. of Dosage Form Design*, M. E. Aulton, 341–358, 1988.

*Primary Examiner*—V. Millin
*Assistant Examiner*—Eric P. Raciti
*Attorney, Agent, or Firm*—Townsend and Townsend and Crew LLP

[57] ABSTRACT

The invention provides methods and apparatus for the delivery of therapeutic liquids to the respiratory system of a patient. In an exemplary embodiment, the apparatus includes a vibratable non-planar member having tapered apertures which produce droplets wherein about 70% of more of the droplets by weight have a size in the range from about 1 μm to 6 μm. The apparatus may further optionally include a breath sensor which detects the inspiratory flow rate and transmits a signal to vibrate the non-planar member at a frequency corresponding to the inspiratory flow rate. Optionally, the non-planar member may be included in a disposable mouthpiece assembly that is separate from the oscillator assembly. In this manner, the mouthpiece assembly may be discarded after use, while the oscillator assembly may be reused.

47 Claims, 5 Drawing Sheets

APPARATUS AND METHODS FOR THE DELIVERY OF THERAPEUTIC LIQUIDS TO THE RESPIRATORY SYSTEM

BACKGROUND OF THE INVENTION

1. Field of the Invention

This invention relates generally to the field of therapeutic drug delivery, and in particular to the delivery of therapeutic liquids to the respiratory system.

A wide variety of procedures have been proposed to deliver a drug to a patient. Of particular interest to the present invention are drug delivery procedures where the drug is in liquid form and is delivered to the patient's lungs. Effective intrapulmonary drug delivery depends on a variety of factors, some of which can be controlled by the clinician or scientist and others that are uncontrollable. Uncontrollable factors include, among others, the airway geometry of the patient's respiratory tract and lung and other respiratory diseases. Of the controllable factors, two are of particular interest. The first is the droplet size and droplet size distribution. The second is the breathing pattern.

A major factor governing the effectiveness of drug deposition in the lungs is the size of the inspired particles. Depending on the particle size, total deposition in various regions of the lung may vary from 11% to 98%. See Heyder et al., *Aerosol Sci.*, 1986, 17, 811–825, the disclosure of which is herein incorporated by reference. Therefore, proper selection of particle size provides a way to target liquid droplets to a desired lung region. It is particularly difficult, however, to generate a liquid spray in which all the droplets will have the same size or the same aerodynamic behavior such that drug deposition in the desirable lung region is predictable.

A parameter that may be used to define droplet size is the respirable fraction (RF). The respirable fraction (RF) is defined as the fraction of the mass of aerosol droplets falling between a particular size range, usually in the range from about 1 µm to 6 µm. See D.C. Cipolla, et al., *Assessment of Aerosol Delivery Systems for Recombinant Human Deoxyribonuclease*, S.T.P. Pharma Sciences 4(1) 50–62, 1994, the disclosure of which is herein incorporated by reference. As used hereinafter, the term respirable fraction (RF) will include the percentage of droplets having sizes falling in the range of from about 1 µm to 6 µm. Another parameter that may be used to evaluate nebulization performance is the efficiency (E). The efficiency (E) of a nebulizer is the amount of liquid which is actually aerosolized and leaves the nebulizer in aerosolized form as compared to the amount of liquid that is initially supplied to the nebulizer. See D.C. Cipolla, et al., *Assessment of Aerosol Delivery Systems for Recombinant Human Deoxyribonuclease*, S.T.P. Pharma Sciences 4(1) 50–62, 1994. Still another parameter that may be used to measure the performance of nebulizers is the delivery percentage (D) which is the respirable fraction (RF) multiplied by the efficiency (E). See D.C. Cipolla, et al., *Assessment of Aerosol Delivery Systems for Recombinant Human Deoxyribonuclease*, S.T.P. Pharma Sciences 4(1) 50–62, 1994.

A variety of inhalation devices have been proposed including air jet nebulizers, ultrasonic nebulizers, and metered dose inhalers (MDIs). Air jet nebulizers usually utilize a high pressure air compressor and a baffle system that separates the small particles from the spray. Ultrasonic nebulizers generate ultrasonic waves with an oscillating piezoelectric crystal to produce liquid droplets. Another type of ultrasonic nebulizer of interest is described in U.S. Pat. Nos. 5,261,601 and 4,533,082. This nebulizer includes a housing that defines a chamber for holding a quantity of liquid to be dispensed. A perforated membrane is held over the chamber and defines a front wall of the chamber, with the rear surface of the membrane being in constant contact with the reservoir of liquid held in the chamber. The apparatus further includes an ultrasonic vibrator connected to the housing to vibrate the perforated membrane. Typical MDIs usually employ a gas propellant, such as CFC, which carries the therapeutic substance and is sprayed into the mouth of the patient.

Most commercially available inhalers produce sprays having a respirable fraction (RF) of 80% or less, with ultrasonic nebulizers usually having a respirable fraction (RF) of less than about 50%, thereby making dosing control difficult and inaccurate. Presently, most commercially available inhalers also have a poor efficiency (E), usually less than about 60%. See D.C. Cipolla, et al., *Assessment of Aerosol Delivery Systems for Recombinant Human Deoxyribonuclease*, S.T.P. Pharma Sciences 4(1) 50–62, 1994. Such inefficiency often results from the construction of the nebulizer since a certain amount cannot be nebulized and remains within the device. Since most commercially available nebulizers have both a poor respirable fraction (RF) and a poor efficiency (E), the delivery percentage (D) is also poor. Therefore, such inhalers have generally not been used for delivery of drugs that have potent therapeutic agents such as hormones and peptides or other drugs having a high level of toxicity and which can be expensive.

The second factor influencing droplet deposition is the patient's breathing pattern. Inhalation flow rate affects the probability of particle impact, while tidal volume and lung volume affect particle residence time in each lung region. Therefore, effective droplet deposition should be adaptable to the inhalation flow rate as well as the patient's tidal volume and lung volume.

Other important factors often considered when designing an effective therapeutic drug delivery system include both cost and convenience. When nebulizing the medicament, the apparatus involved usually comes in contact with the medicament. Hence, the apparatus will need to be sterilized before reuse, or discarded. However, sterilization may not be convenient for a hand held portable device. Disposal can also be expensive, particularly when the apparatus includes a piezoelectric crystal for nebulizing the liquid.

It would therefore be desirable to provide improved apparatus and methods for the delivery of liquids to the respiratory system. Such apparatus and methods should be capable of producing a spray which may predictably be deposited in selected regions of the lungs. Further, it would be desirable if such a spray were produced from a small volume of liquid. Moreover, it would be desirable if the apparatus and methods provided for a controlled drug delivery rate, preferably being based on the rate of inspiratory air flow generated during inhalation. Finally, it would be desirable if such methods and devices were inexpensive, efficient, and easy to use.

2. Brief Description of the Background Art

U.S. Pat. No. 4,533,082 describes a vibrating orifice apparatus with a multiplicity of apertures for producing liquid droplets.

As previously described, U.S. Pat. No. 5,261,601 describes an atomizer having a membrane covering a liquid chamber.

Apparatus for atomizing liquids such as liquid fuel, water, liquid drugs are described in U.S. Pat. Nos. 3,812,854;

4,159,803; 4,300,546; 4,334,531; 4,465,234; 4,632,311; 4,338,576; and 4,850,534.

D.C. Cipolla, et al., *Assessment of Aerosol Delivery Systems for Recombinant Human Deoxyribonuclease*, S.T.P. Pharma Sciences 4(1) 50–62, 1994, previously incorporated by reference, describes various inhalation devices and provides selected data on their efficiency (E) and respirable fraction (RF) values.

SUMMARY OF THE INVENTION

The present invention provides methods and apparatus for the delivery of therapeutic liquids to the respiratory system of a patient. In one exemplary embodiment, the apparatus of the present invention is characterized in that it is able to produce a spray having a respirable fraction (RF) of greater than about 70%, preferably more than about 80%, and most preferably more than about 90%. Preferably, the apparatus will eject the liquid at a flow rate of at least about 5 μl/sec, and preferably more than about 10 μl/sec. By producing such a spray, the aerodynamic behavior of all the droplets will be substantially the same, thereby enabling the apparatus to be useful in intrapulmonary drug delivery.

The apparatus will preferably include a vibratable non-planar surface or non-planar member with apertures extending therethrough. The non-planar member will preferably comprise a rigid thin shell member having a front surface, a rear surface, and a plurality of apertures extending therebetween. The apertures are tapered so that they narrow from the rear surface to the front surface. A liquid supplier is provided which delivers liquid to the rear surface such that substantially all of the delivered liquid adheres to the thin shell member, and particularly within the large opening of the tapered apertures, by surface tension, i.e. in surface tension contact. A vibrator is further provided which vibrates the thin shell member to eject liquid droplets from the front surface of the thin shell member. Preferably, the apertures will be configured to eject liquid droplets having a respirable fraction (RF) of greater than about 70%, preferably more than about 80%, and most preferably more than about 90%. In another preferable aspect, the apparatus will have an efficiency (E) at or closely approaching 100%, i.e. substantially all liquid supplied to the rear surface will be aerosolized and will be available for inhalation. In this way, the delivery percentage (D) will usually be about the same as the respirable fraction (RF), i.e. greater than about 70%.

In one exemplary aspect, the size of the apertures at the front surface is in the range from about 1 μm to 6 μm, with the apertures have a slope at the front surface of about 10° or greater relative to a central axis of the apertures, preferably being in the range from about 10° to 20° relative to the central axis of the apertures, and more preferably being in the range from about 10° to 15° relative to the central axis. Preferably, the thin shell member will have a thickness of about 50 μm to about 100 μm, more preferably from about 75 μm to about 100 μm which provides the thin shell member with sufficient rigidity to vibrate in unison and provides sufficient aperture volume. In the present invention, ejection of droplets is developed due to the solid/fluid interaction inside the aperture, i.e. the interaction of the liquid against the tapered wall of the aperture. The cross sectional geometry of the aperture is therefore important. For example, if the aperture has a straight cylindrical wall with a slope of 0° relative to the central axis (or a 90° slope relative to the front surface of the thin shell member), ejection will not occur. Instead, the vibratory motion will cause the liquid to break loose from the vibratory surface so that it will not eject through the aperture.

For apertures smaller than 6 μm, the slope near the exit opening of the aperture is particularly important because the discharge coefficient of such an aperture is substantially smaller than for larger apertures. For apertures smaller than 6 μm, a slight variation in the slope near the small opening of the aperture will make significant influence on ejection of droplets because the tapered shape near the opening increases the surface area that is subjected to solid/fluid interaction near the exit opening. For example, vibration of the thin shell member when the apertures have a slope of 20° (relative to the central axis of the apertures) near the small opening produces 10 times more droplets than when the apertures are at right angles to the front surface. In this manner, a high flow rate can be achieved using a small thin shell member. A small thin shell member is desirable in that it has higher structural rigidity which assists in producing a fine spray as described hereinafter.

In another exemplary aspect, the thin shell member is hemispherical, parabolic, arc shaped, or curved in geometry, with the large opening of each aperture being located at the concave side, and the small opening of each aperture being located at the convex side. The thin shell member is preferably formed to have a low mass and a very high stiffens which causes the thin shell member to oscillate as a rigid body, i.e. homogeneously. In this way, all the apertures in the thin shell member are subject to the same amplitude so that droplets may be produced with a uniform size and with a desired respiratory fraction.

In one particular embodiment, the invention provides an apparatus for nebulizing a liquid having a housing with a proximal end and a distal end. A non-planar member, and preferably a thin shell member, is mounted within the housing, with thin shell member having a plurality of apertures for nebulizing the liquid upon vibration of the thin shell member. A vibrator is provided and is removably attached about the housing which vibrates the thin shell member. Preferably, the thin shell member is mounted within a dynamically isolated portion of the housing. In this manner, the vibration is not transmitted to the housing allowing the vibrator to be dismantled and reinstalled over the housing as desired.

Advantageously, the elements that come in contact with the mouth of the patient or with of the therapeutic liquid are held within the housing. Prior to use, the housing is connected to the vibrator which transmits vibratory motion to the thin shell member inside the housing to produce ejection of droplets which are then entrained in the inspiratory air flow. In this manner, the vibrator will not come into contact with the liquid, thereby allowing the vibrator to be reused with a new and uncontaminated housing. Such a configuration provides an economical nebulizing apparatus since the relatively expensive vibrator may be reused.

In a further exemplary embodiment of the present invention, an apparatus is provided which ejects a liquid spray at a rate synchronized with the inspiratory flow created during inhalation so the that ejection rate is proportional to the inspiratory flow rate. The apparatus includes a housing having a distal end and a mouthpiece at a proximal end. A non-planar member, and preferably a thin shell member, is mounted within the housing, with the thin shell member having a plurality of apertures. A vibrator is provided to vibrate the thin shell member and to eject liquid from the apertures. An acoustic chamber is provided within the housing which produces an audible signal during inhalation from the mouthpiece. Further provided is a controller for controlling the rate of thin shell member vibration upon detection of the audible signal. Preferably, the controller includes a microphone which detects the audible signal so that an electrical signal may be sent to the vibrator.

In this manner, the patient may simply breath through the mouthpiece (or a nasal adapter) to control the rate of droplet production. The respiratory flow passes through the acoustic chamber which produces the acoustic tone which is proportional to the inspiratory flow rate. Thus, the frequency of the acoustic tone indicates the inspiratory flow rate at any instant of the breathing cycle. Integration of the flow rate with time produces the tidal volume. Both the flow rate and the tidal volume can then be used to determine when the ejector should eject droplets and at what mass flow rate such that maximum deposition of droplets is obtained. Further, the acoustic tone may be recorded to produce a record of the breathing pattern of the patient which may be stored in a microprocessor. This information can be later used to synchronize the ejection of droplets for the same patient. Such information may also be later employed for other diagnostic purposes.

The invention further provides a method for nebulizing a liquid. According to the method, a non-planar member, preferably a thin shell member, having a plurality of tapered apertures extending therethrough is vibrated. The apertures in the thin shell member are configured to produce liquid droplets having a respirable fraction (RF) of greater than about 70%, preferably more than about 80%, and most preferably more than about 90%. In a preferable aspect, liquid is supplied to the thin shell member such that substantially all of the delivered liquid adheres to the thin shell member by surface tension. In this manner, the need for a container or a chamber to hold the liquid against the thin shell member is eliminated. Instead, the liquid is open to the atmosphere and is not subjected to pressurization or reflecting acoustic waves that may be produced within an adjacent chamber. Preferably, liquid will be supplied to the thin shell member by squeezing a liquid reservoir which dispenses a discrete volume of liquid onto the thin shell member. Usually, substantially all liquid delivered to the thin shell member will be transformed into liquid droplets that are available for inhalation, i.e. the efficiency (E) will be at or near 100%. In this way, the delivery percentage (D) will be substantially the same as the respirable fraction (RF).

In another aspect, the method provides for producing the liquid droplets at a rate greater than about 5 µliters per second. In another aspect, the vibrating step further comprises vibrating substantially all of the apertures in the thin shell member in unison. Preferably, the thin shell member will be vibrated at a frequency in the range from about 45 kHz to 200 kHz. In yet another aspect, the thin shell member is held within a housing having a mouthpiece, and the thin shell member is vibrated at a rate corresponding to an inspiratory flow rate through the mouthpiece. In one preferable aspect, the thin shell member is vibrated only during inhalation from the mouthpiece. Control of shell member vibration in this manner may be accomplished by producing an audible signal during inhalation and detecting the produced signal.

In one particular aspect, the vibrating step comprises removably attaching a vibrating source about a housing enclosing the thin shell member and actuating the vibrating source. Optionally, the vibrating source may be removed from the housing and the housing discarded after use.

The invention provides a further exemplary method for delivering a liquid to the lungs of a patient. According to the method, a housing is provided having a proximal end and a distal end. Liquid is supplied to an thin shell member disposed within the housing, with the thin shell member having a plurality of tapered apertures extending therethrough. The patient then inhales from the proximal end of the housing at a selected inspiratory flow rate, and the thin shell member is vibrated to eject the liquid at a rate corresponding to the inspiratory flow rate.

In one aspect of the method, the inspiratory flow rate is variable. In another aspect, the vibrating step further comprises ejecting the liquid only during inhalation. In still a further aspect, an audible signal is produced during inhalation and the produced signal is detected to control the rate of vibration of the thin shell member.

The thin shell member will preferably be vibrated to produce liquid droplets having a respirable fraction (RF) of greater than about 70%, preferably more than about 80%, and most preferably more than about 90%. In another preferable aspect, liquid will be supplied to the thin shell member such that substantially all of the delivered liquid adheres to the thin shell member by surface tension. Preferably, substantially all of the apertures in the thin shell member will be vibrated in unison.

DETAILED DESCRIPTION OF THE SPECIFIC EMBODIMENTS

Figure 2:
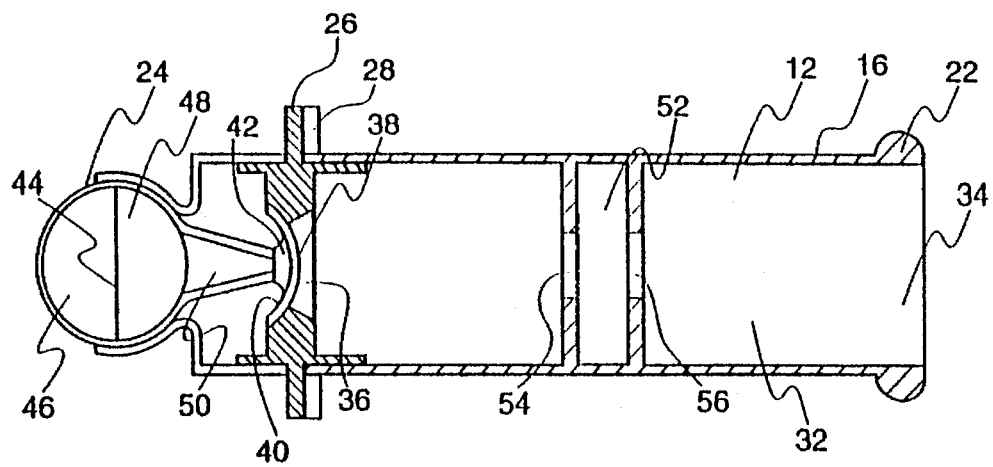
FIG. 2 is a cross-sectional view of the mouthpiece assembly of FIG. 1.

The invention provides methods and apparatus for producing a very fine spray useful in pulmonary drug delivery procedures. The invention provides for producing a spray having a respirable fraction (RF) of greater than about 70%, preferably more than about 80%, and most preferably more than about 90%. The efficiency (E) of the nebulization apparatus will usually be at or near 100%, leading to a delivery percentage (D) which is substantially the same as the respirable fraction (RF). Such a spray will preferably be produced at a flow rate of at least about 5 µl per second, and more preferably at least about 10 µl per second. In this manner, a spray of a selected size is produced where the aerodynamic behavior of all the droplets is substantially the same, thereby enabling the spray to be predictably deposited in selected regions of the lungs during intrapulmonary drug delivery procedures.

The invention may be employed to deliver a wide variety of drugs to the respiratory system, and will preferably be used to deliver drugs having potent therapeutic agents, such as hormones, peptides, and other drugs requiring precise dosing. Liquid drugs which may be nebulized using the present invention include drugs in solution form (e.g., in aqueous solution, ethanol solution, aqueous/ethanol mixture solution, and the like), in colloidal suspension form, and the like.

The invention will preferably be configured to supply the spray upon demand, i.e., the spray will be produced and delivered only upon inhalation by the patient. Further, such a spray will preferably be produced and delivered at a rate corresponding to the inhalation or inspiratory flow rate produced by the patient when inhaling the spray. In this manner, the spray will be produced only when the patient is inhaling, and will preferably be produced at a rate corresponding to the inhalation rate.

The invention will provide such a spray by providing the liquid to a vibratable non-planar member, which is preferably a thin shell member having a plurality of apertures. Liquid is preferably supplied to the thin shell member such that substantially all of the delivered liquid will adhere to the thin shell member by surface tension. Upon vibration of the thin shell member, the adhering liquid will be ejected through the apertures to form the fine spray. In this manner, a precise and controlled amount of liquid drug can be supplied to the thin shell member for nebulization, thereby eliminating the need for a fluid reservoir to be placed against the thin shell member.

Apertures in the thin shell member of the invention will preferably be tapered in geometry, with the smaller end of the aperture being located at a front surface of the thin shell member and the larger opening of the aperture being at the rear surface of the thin shell member. The size of the apertures at the front surface will preferably be in the range from about 1 µm to 6 µm, with the slope of the apertures at the front surface being in the range from about 10° or greater relative to a central axis extending through the apertures, preferably from about 10° to 20° relative to the central axis extending through the apertures, and more preferably being in the range from about 10° to 15° relative to the central axis.

Figure 1:
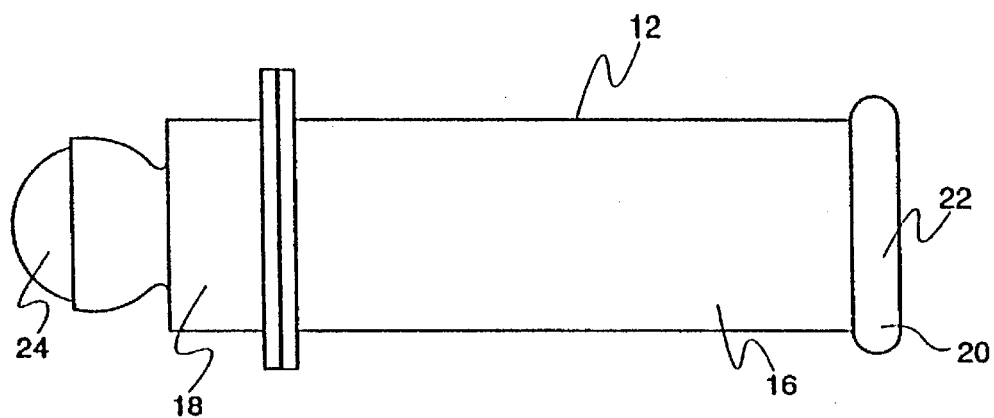
FIG. 1 is a top view of a disposable mouthpiece assembly of a nebulizing apparatus according to the present invention.
Figure 3:
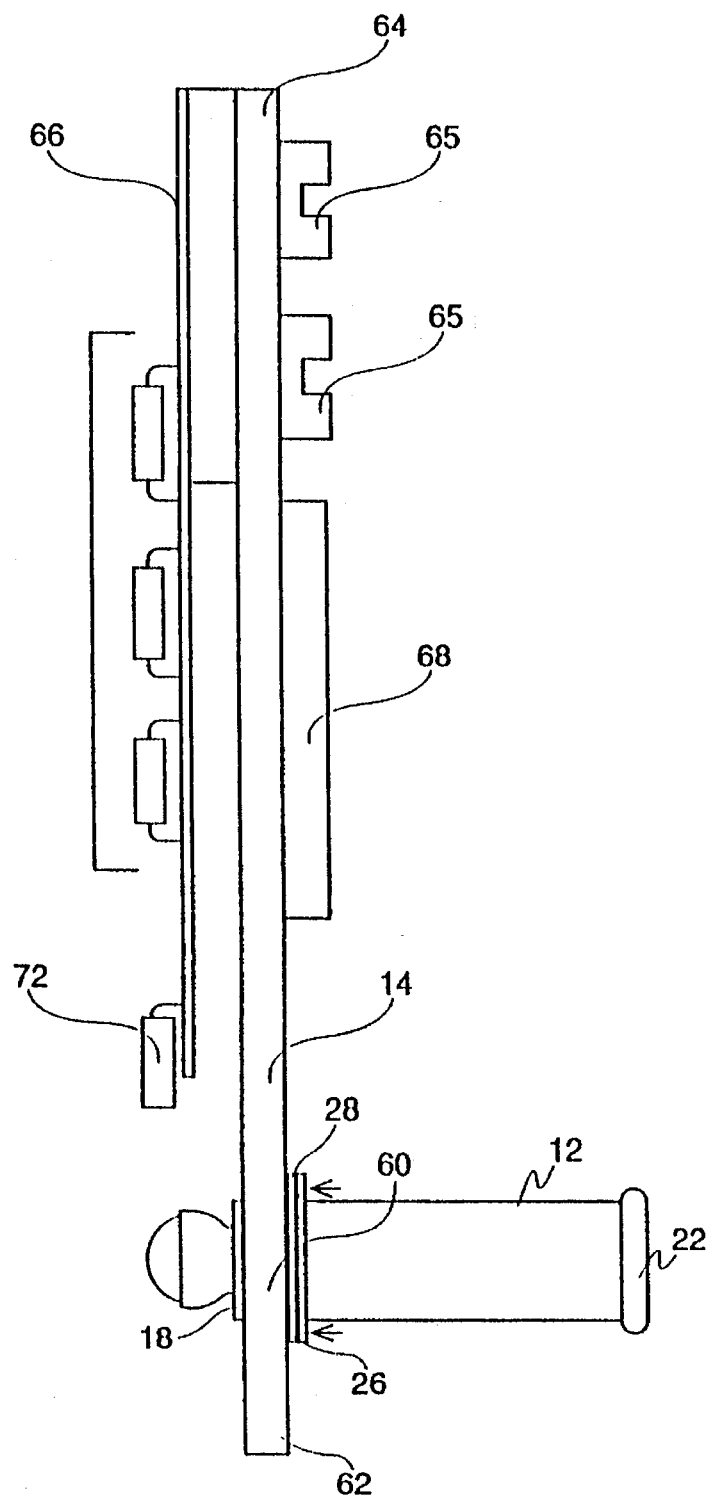
FIG. 3 is a side view of an exemplary nebulizing apparatus having an oscillator assembly attached about the mouthpiece assembly of FIG. 1 according to the present invention.

Referring now to the figures, an exemplary embodiment of a nebulizing apparatus 10 will be described. As best illustrated in FIG. 3, the nebulizing apparatus 10 includes a disposable mouthpiece assembly 12 and a removable oscillating assembly 14. Referring to FIG. 1, construction of the mouthpiece assembly 12 will be described. The mouthpiece assembly 12 includes an elongate tubular housing 16 having a proximal end 18 and a distal end 20. At the distal end 20 is a mouthpiece 22, while a liquid supply cartridge 24 is at the proximal end 18. As will be described in grater detail hereinafter, a carrier plate 26 extends from the housing 16 and is provided to hold a thin shell member within the housing 16. An elastomeric 0-ring 28 is placed adjacent the carrier plate 26 and is positioned against a vibrating beam as described in greater detail hereinafter. To dynamically isolate the carrier plate 26, the housing 12 is preferably constructed of an elastomeric material, preferably having a modulus of elasticity of about 100 psi to 150 psi.

Referring to FIG. 2, the interior of the mouthpiece assembly 12 will be described. The tubular housing 16 forms a central chamber 32 having an opening 34 at the mouthpiece 22. Annularly extending into the central chamber 32 is the carrier plate 26. In turn, the carrier plate 26 is attached about a thin shell member 36 having a front surface 38 and a rear surface 40. Extending between the front surface 38 and rear surface 40 are a plurality of tapered apertures (not shown) having the smaller opening at the front surface 38 and the larger opening at the rear surface 40. Upon vibration of the carrier plate 26, the thin shell member 36, is vibrated so that liquid may be ejected through the apertures and from the front surface 38 as described hereinafter.

An amount of liquid 42 is supplied to the rear surface 40 from the liquid supply cartridge 24. The liquid cartridge 24 includes a divider 44 that separates the liquid supply cartridge 24 into an air volume 46 and a liquid volume 48. To dispense liquid from the liquid volume 48, the liquid supply cartridge 24 is squeezed to force liquid in the liquid volume 48 through a nozzle 50 where it comes into contact with the rear surface 40 of the thin shell member 36. The cartridge 24 becomes permanently deformed when squeezed so that the liquid 42 delivered to the rear surface 40 will not be withdrawn back into the liquid volume 48. The size of the air volume 46 will be configured such that all of the liquid within the liquid volume 48 will be transferred from the liquid volume 48 when the cartridge 24 is squeezed.

The liquid 42 delivered from the supply cartridge 24 will usually be held to the rear surface 40 solely by surface tension forces. In this way, the liquid 42 may remain in contact with the rear surface 40 until ejected and without the need for a separate chamber to hold the liquid 42 against the rear surface 40. To eject the liquid 42 from the front surface 38, the carrier plate 26 is vibrated to in turn vibrate the thin shell member 36. The liquid 42 adhering to the rear surface then passes through the apertures and from the front surface 38 as described in U.S. Pat. No. 5,164,740 and copending application Ser. Nos. 08/163,850 and 08/417,311, the entire disclosures of which are herein incorporated by reference.

The thin shell member 36 is preferably formed of a thin, rigid material having a hemispherical geometry. Alternatively, the thin shell member 36 may be parabolic, arc shaped, or curved in geometry. The thin shell member 36 will have a very high bending stiffness which will allow it to follow the vibratory motion of the carrier plate 26 as a rigid body. In this way, the entire thin shell member 36 will vibrate in unison so that all apertures are subject to the same amplitude of vibration. Such vibration will assist in ejecting uniformly sized droplets (i.e. having a respirable fraction (RF) of greater than about 70%, preferably more than about 80%, and most preferably more than about 90%) simultaneously from most or all of the apertures. The spray produced by the thin shell member 36 is dispensed into the central chamber 32 in the direction of the opening 34. In this manner, as the patient inhales from the mouthpiece 22, the spray within the central chamber 32 will be drawn into the patient's lungs.

Figure 8:
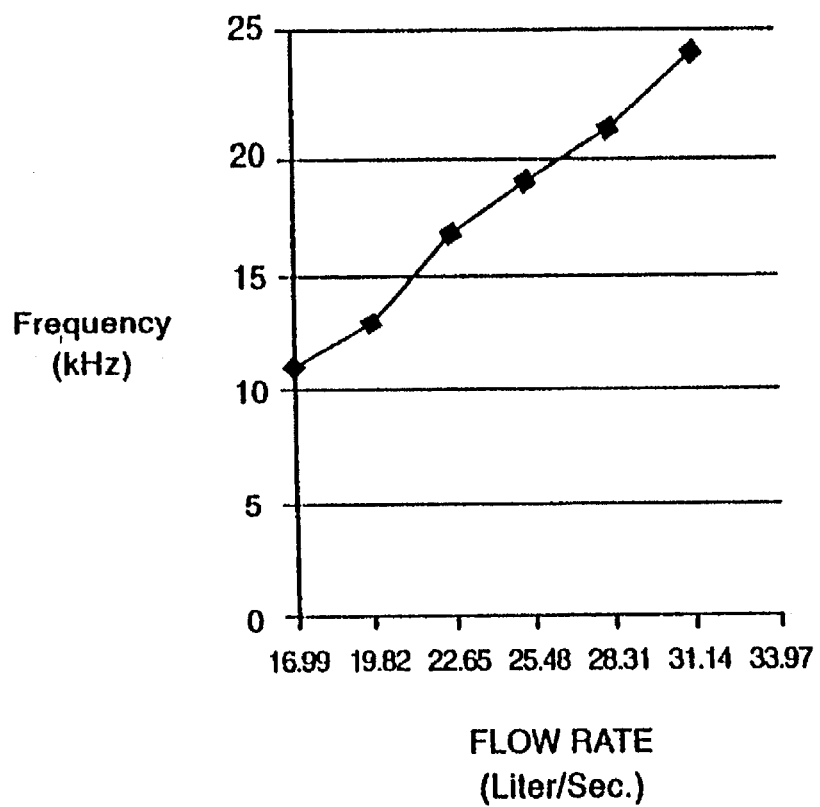
FIG. 8 is a graph illustrating the relationship between the acoustic frequency produced by an acoustic chamber within the mouthpiece assembly of FIG. 1 and the inspiratory flow rate through the mouthpiece assembly according to the present invention.

To control the time and/or rate at which the spray is produced, the mouthpiece assembly 12 further includes an acoustic chamber 52 having holes 54 and 56. Upon inhalation, air within the central chamber 32 passes through the holes 54 and 56 to produce an acoustic tone. This tone may be detected as described in greater detail hereinafter and used to determine both when the patient is inhaling and the patient's inspiratory flow rate. Such a signal may then be used to actuate the oscillating assembly which vibrates the thin shell member 36. Such a signal may be employed to control the time at which the shell member 36 is vibrated, e.g., such as only during inhalation. Alternatively, such a signal may also be employed to vibrate the thin shell member 36 at a frequency corresponding to the inspiratory flow rate. FIG. 8 illustrates one example of acoustical frequencies that may be produced for various inspiratory flow rates. For instance, an inspiratory flow rate of about 20 liters per second will generate an acoustical frequency of about 15 kHz. In turn, the detected frequency may be employed to drive the thin shell member 36.

Referring now to FIG. 3, operation of the combined mouthpiece assembly 12 and the oscillating assembly 14 will be described. The mouthpiece assembly 12 will preferably be constructed so that it may be removably attached to the oscillating assembly 14. In this manner, the mouthpiece assembly 12 may be discarded after use, while the oscillating assembly 14 which will not come into contact with the liquid may be reused. One particular advantage of such a configuration is that the mouthpiece assembly 12 may be constructed relatively inexpensively by not including an internal oscillator. Since the oscillating assembly 14 may be reused, costs to the patient are reduced.

Figures 4, 5:
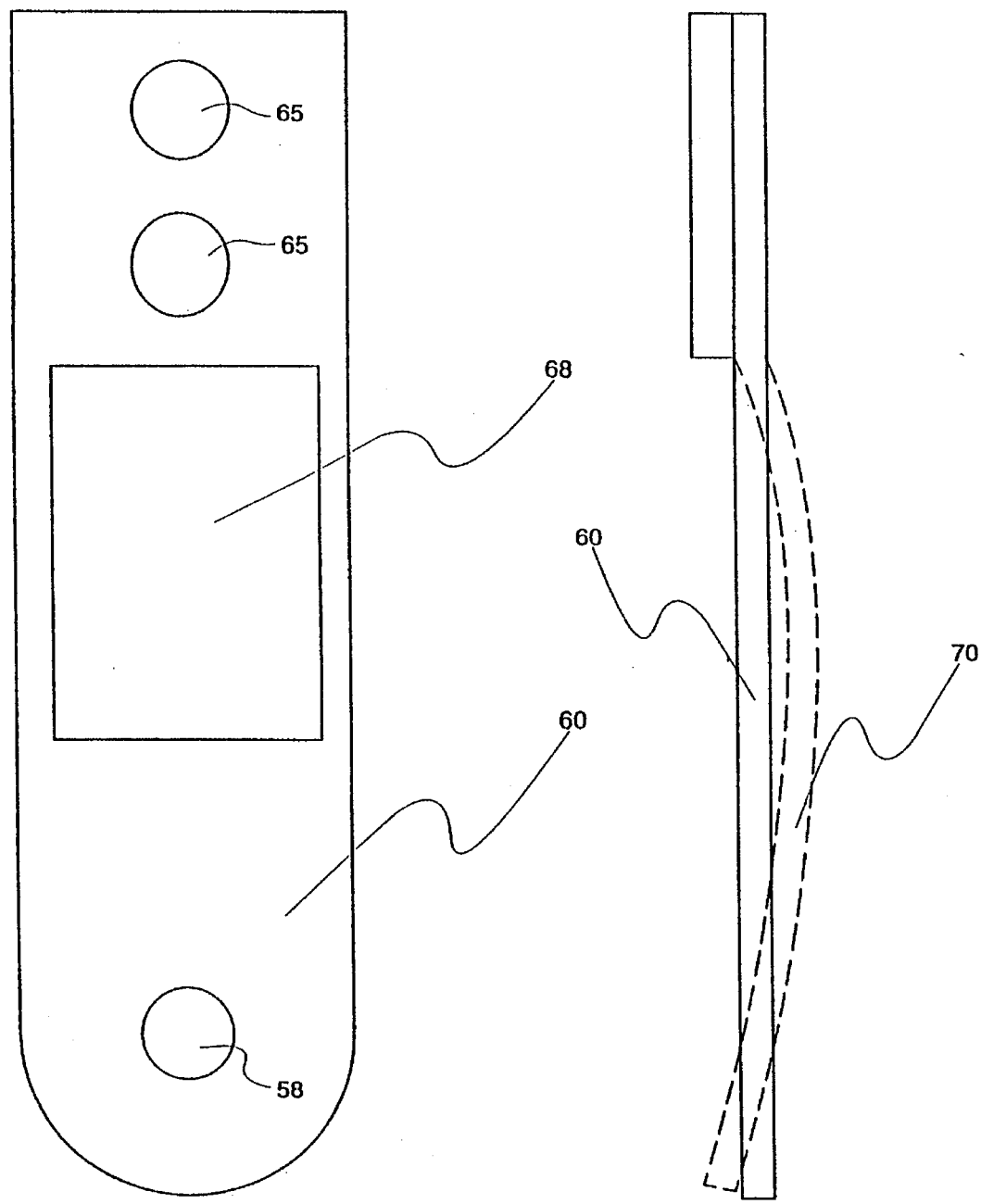
FIG. 4 is a bottom view of a vibratory cantilever beam of the oscillator assembly of FIG. 3.
FIG. 5 illustrates a side view of the cantilever beam of FIG. 4, with the mode of vibration being shown in phantom line.

The mouthpiece assembly 12 is connected to the oscillating assembly 14 by sliding the proximal end 18 of the mouthpiece assembly 12 through an opening 58 (see FIG. 5) in a cantilever beam 60 of the oscillating assembly 14 until the O-ring 28 engages and is secured against the cantilever beam 60 as indicated by the arrows. A latching mechanism (not shown) may optionally be provided to removably latch the mouthpiece assembly 12 to the cantilever beam 60.

The cantilever beam 60 is provided with a free end 62 and a fixed end 64. The fixed end 64 is attached to an electronic circuit board 66 by a pair of screws 65, thus limiting the ability of the fixed end 64 to vibrate. On the other hand, the free end 62 which is attached to the mouthpiece assembly 12 is free to vibrate. A piezoelectric element 68 is bonded to the beam 60 and transmits vibratory motion to the beam 60. The dimensions of the beam 60 may be varied depending on the frequency of vibration. In one particular embodiment which is usually vibrated at 45 kHz to 200 kHz, the beam 60 will preferably have a length of about 30 mm to 80 mm, preferably at about 40 mm, a width of about 8 mm to 15 mm, preferably at about 12 mm, and a thickness of about 0.5 mm to 1 mm, preferably at about 0.7 mm. Such a beam will preferably be oscillated at a frequency of about 45 kHz which corresponds to the natural frequency of the beam. When vibrated, the beam 60 will have an oscillation mode shape 70 as illustrated in phantom line in FIG. 5.

Upon vibration of the cantilever beam 60, the elastomeric material of the housing 16 prevents transfer of vibratory energy through the tubular housing 16. In this manner, only the carrier plate 26 and the adjacent portion of the housing 16 are vibrated so that only minimal energy is needed to sufficiently vibrate the thin shell member 36. The cantilever beam 60 will preferably be vibrated to produce an oscillation amplitude of about 0.001 mm at the free end 62. Such vibration is transferred to the thin shell member 36 via the carrier plate 26 to produce a fine spray particles having a desired respirable fraction (RF).

In one experiment, the apparatus 10 of FIG. 3 was vibrated at a frequency of 45 kHz, and the particle size and distribution was measured by a particle sizer commercially available from Malvern Instruments Inc. (Southburrow, MA). The results indicated that about 94.99% of the particles were in the range from 1 to 6 micron with a flow rate of about 10 cubic μl per second.

To operate the nebulizing apparatus 10, the patient first attaches the mouthpiece assembly 12 to the oscillating assembly 14 as previously described. The liquid supply cartridge 24 is then squeezed to transfer the liquid to the rear surface 38 of the thin shell member 36. The patient then places his mouth over the mouthpiece 22 and begins to inhale. As air is drawn through the central chamber 32, an acoustic tone is produced by the acoustic chamber 52. As illustrated in FIG. 3, the acoustic tone may be detected by a microphone 72 on the circuit board 66. The detected acoustic signal is then processed by the circuit board 66 and is used to drive the piezoelectric element 68 at a frequency proportional to the acoustical frequency. In this manner, spray begins to eject from the thin shell member 36 upon inhalation, and at a rate that is proportional to the inspiratory flow rate. After the patient has fully inhaled, the acoustic signal ceases, thereby ceasing vibration of the piezoelectric element 68. If all of the liquid has not been dispensed, the patient may again inhale as previously described until all of the liquid has been delivered to the patient's lungs.

Figure 6:
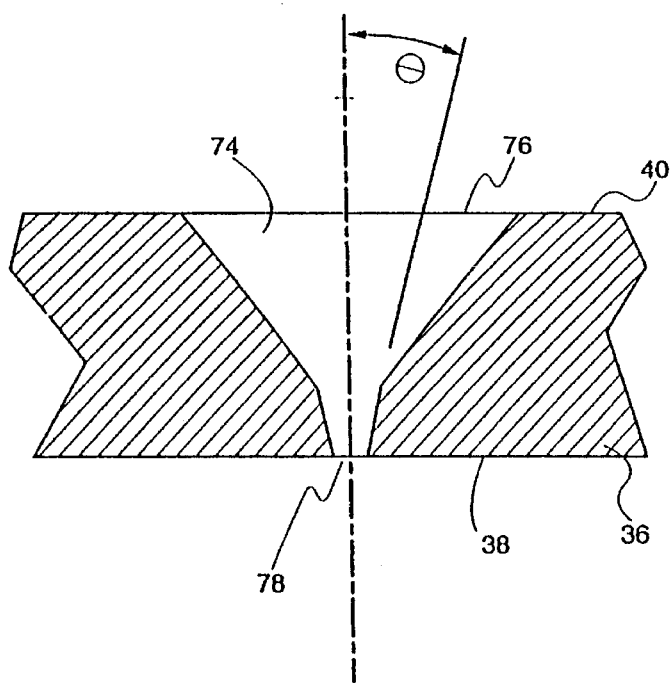
FIG. 6 is a cross-sectional side view of an exemplary aperture in a thin shell member according to the present invention.

Referring to FIG. 6, an exemplary embodiment of an aperture 74 that may be included in the thin shell member 36 will be described. The aperture 74 has a conical shape, with a large opening 76 being at the rear surface 40 and a small opening 78 being at the front surface 38. At the small opening 78, the aperture 74 will have a slope, θ, measured relative to a central axis extending through the aperture 74. The slope θ at the small opening 78 will preferably be in the range from about 10° to 20° more preferably in the range from about 10° to 15° and most preferably at about 15°. As the aperture 74 approaches the large opening 76, the slope may increase as illustrated. Preferably, the slope of the aperture 74 at the large opening 76 will be about 45° relative to the central axis, although the angle is not as critical as near the small opening. The slope of the aperture 74 near the small opening 78 is particularly important since ejection from the thin shell member 36 will occur at the front surface 36 where the small opening 78 is located. The slope, θ, should usually be at least about 10° with respect to the axis of the aperture to insure optimal ejection.

Figure 7:
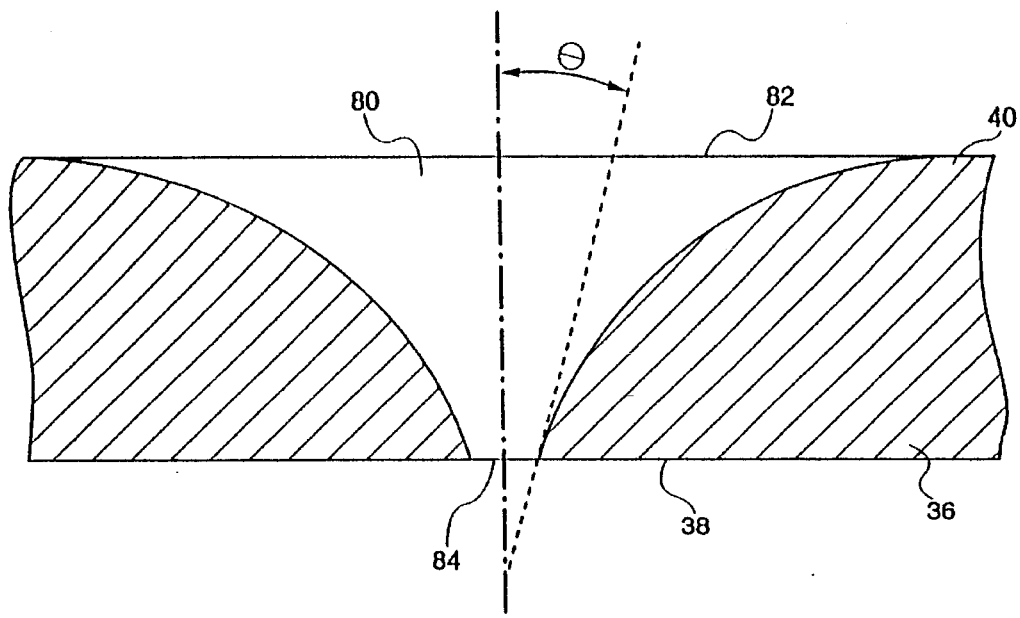
FIG. 7 is a cross-sectional side view of an alternative aperture in a thin shell member according to the present invention.

Referring to FIG. 7, an alternative aperture 80 for the thin shell member 36 will be described. The aperture 80 is conical and has a large opening 82 at the rear surface 40 and a small opening 84 at the front surface 38. When viewed in cross-section, the aperture 80 is formed of portions of two circles, with each circle having the same radius. The circles are positioned so that the slope θ at the small opening 84 will be in the range from about 10° to 20° relative to the central axis, more preferably from about 10° to 15° and most preferably at about 12°. When the small opening 84 is sized at about 3 microns and has a taper of about 12° the ejection rate from the small opening 84 is approximately 100 times greater than a quadrant-edge aperture having a 0° slope at the small opening as described in Jorissen, A.L., *Discharged Measurement at Low Reynolds Number*, ASME, February 1956, pp. 365–368, the disclosure of which is herein incorporated by reference.

Although the foregoing invention has been described in detail for purposes of clarity of understanding, it will be appreciated that certain changes and modifications may be practiced within the scope of the appended claims.

What is claimed is:

1. An apparatus for nebulizing a liquid, the apparatus comprising:

a non-planar member comprising a front surface, a rear surface, and a plurality of apertures extending therebetween, said apertures being tapered to narrow from the rear surface to the front surface;

a liquid supplier which delivers liquid to the rear surface such that substantially all of the delivered liquid adheres to the non-planar member by surface tension; and a vibrator which vibrates the non-planar member to eject liquid droplets from the front surface of the member.

2. An apparatus as in claim 1, wherein the apertures have a preferred geometry to eject liquid droplets such that about 70% of more of the droplets by weight have a size in the range from about 1 to 6 μm.

3. An apparatus as in claim 1, wherein the size of the apertures at the front surface is in the range from about 1 μm to 6 μm, and wherein the apertures have a slope at the front surface in the range from about 10° to 20° relative to a central axis extending through the apertures.

4. An apparatus as in claim 3, wherein the slope of the apertures at the front surface is in the range from about 10° to 15° relative to the central axis.

5. An apparatus as in claim 1, wherein the slope of the apertures at the front surface is about 12° relative to the central axis.

6. An apparatus as in claim 1, wherein the non-planar member is sufficiently rigid to vibrate homogeneously.

7. An apparatus as in claim 1, wherein the non-planar member is a thin shell member having a shape selected from the group of shapes consisting of an arc shape, a parabolic shape, or a hemispherical shape.

8. An apparatus as in claim 1, further comprising a housing having a proximal end and a distal end, wherein the non-planar member is held within the housing, and wherein the vibrator is removably attached about the housing.

9. An apparatus for nebulizing a liquid, the device comprising:

a housing having a proximal end and a distal end;

a vibratable non-planar member mounted within the housing, said non-planar member having a plurality of apertures for nebulizing the liquid upon vibration of the non-planar member; and a vibrator removably attached about the housing which vibrates the non-planar member.

10. An apparatus as in claim 9, wherein each of the apertures is tapered in geometry.

11. An apparatus as in claim 10, wherein the tapers have a size in the range from about 1 μm to 6 μm at their narrowest dimension.

12. An apparatus as in claim 9, wherein the non-planar member is mounted within a portion of the housing which is isolated by an elastomeric material.

13. An apparatus as in claim 9, wherein the non-planar member is sufficiently rigid to vibrate homogeneously.

14. An apparatus as in claim 9, wherein the non-planar member is a thin shell member having a shape which is selected from the group of shapes consisting of an arc shape, a parabolic shape, or a hemispherical shape.

15. An apparatus as in claim 9, further comprising a mouthpiece at the proximal end of the housing.

16. An apparatus as in claim 15, further comprising an acoustical chamber within the housing which produces an audible signal during inhalation from the mouthpiece and which may be detected to control the operation of the vibrator.

17. An apparatus for nebulizing a liquid, the apparatus comprising:

a housing having a distal end and a mouthpiece at a proximal end;

an non-planar member mounted within the housing, said non-planar member having a plurality of apertures;

a vibrator which vibrates the non-planar member to eject liquid from the apertures;

an acoustic chamber within the housing which produces an audible signal during inhalation from the mouthpiece; and a controller for controlling the rate of non-planar member vibration upon detection of the audible signal.

18. An apparatus as in claim 17, wherein the controller includes a microphone which detects the audible signal.

19. An apparatus as in claim 17, wherein the non-planar member includes a front surface and a rear surface, with the plurality of apertures extending between the front surface and rear surface, said apertures being tapered to narrow from the rear surface to the front surface.

20. An apparatus as in claim 19, further comprising a liquid supplier which delivers liquid to the rear surface such that substantially all of the delivered liquid adheres to the non-planar member by surface tension.

21. An apparatus as in claim 17, wherein the apertures in the non-planar member are tapered and are constructed to eject liquid droplets from the front surface of the non-planar member such that about 70% of more of the droplets by weight have a size in the range from about 1 μm to 6 μm.

22. An apparatus as in claim 21, wherein the apertures are tapered toward the front surface and are sized to eject liquid droplets such that about 70% of more of the droplets by weight have a size in the range from about 1 μm to 6 μm.

23. An apparatus as in claim 17, wherein the size of the apertures at the front surface is in the range from about 1 μm to 6 μm, and wherein the apertures have a slope at the front surface in the range from about 10° to 20° relative to a central axis extending through the apertures.

24. An apparatus as in claim 23, wherein the slope of the apertures at the front surface is in the range from about 10° to 15° relative to the central axis.

25. A method for nebulizing a liquid, said method comprising:

providing a non-planar member having a plurality of tapered apertures extending therethrough; and vibrating the non-planar member to produce liquid droplets where about 70% of more of the droplets by weight have a size in the range from about 1 μm to 6 μm.

26. A method as in claim 25, further comprising supplying liquid to the non-planar member such that substantially all of the delivered liquid adheres to the non-planar member by surface tension, and wherein substantially all of the delivered liquid is ejected upon vibration of the non-planar member.

27. A method as in claim 26, wherein the supplying step further comprises squeezing a liquid reservoir to supply liquid to the non-planar member.

28. A method as in claim 25, further comprising vibrating the non-planar member at a frequency sufficient to produce the liquid droplets at a rate greater than about 5 μliters per second.

29. A method as in claim 25, wherein the vibrating step further comprises vibrating substantially all of the apertures in the non-planar member in unison.

30. A method as in claim 25, wherein the vibrating step further comprises vibrating the non-planar member at a frequency in the range from about 45 kHz to 200 kHz.

31. A method as in claim 25, wherein the non-planar member is held within a housing having a mouthpiece, and further comprising vibrating the non-planar member at a rate corresponding to an inspiratory flow rate through the mouthpiece.

32. A method as in claim 31, further comprising producing an audible signal during inhalation and detecting the produced signal to control rate of vibration of the non-planar member.

33. A method as in claim 25, further comprising vibrating the non-planar member only during inhalation from the mouthpiece.

34. A method as in claim 25, wherein the liquid is a medicament, and further comprising vibrating the non-planar member to produce liquid droplets such that about 90% of more of the produced droplets by weight have a size in the range from about 1 µm to 6 µm.

35. A method as in claim 25, wherein vibrating step further comprises removably attaching a vibrating source about a housing enclosing the non-planar member and actuating the vibrating source.

36. A method as in claim 35, further comprising removing the vibrating source and discarding the housing.

37. A method for delivering a liquid medicament to the respiratory system of a patient, the method comprising:

providing a housing having a proximal end and a distal end providing a non-planar member which is disposed within the housing, the non-planar member having a plurality of tapered apertures extending therethrough;

supplying liquid to the non-planar member;

inhaling from the proximal end of the housing; and vibrating the non-planar member in response to the inhalation to eject the liquid.

38. A method as in claim 37, further comprising varying the inspiratory flow rate.

39. A method as in claim 37, wherein the vibrating step further comprises ejecting the liquid only during inhalation.

40. A method as in claim 37, further comprising producing an audible signal during inhalation and detecting the produced signal to control the vibration of the non-planar member.

41. A method as in claim 37, wherein the vibrating step further comprises vibrating the non-planar member at a frequency sufficient to produce liquid droplets such that about 70% of more of the droplets by weight have a size in the range from about 1 µm to 6 µm.

42. A method as in claim 37, wherein the supplying step further comprises supplying liquid to the non-planar member such that substantially all of the delivered liquid adheres to the non-planar member by surface tension.

43. A method as in claim 42, wherein the supplying step further comprises dispensing the liquid from a liquid reservoir to supply liquid to the non-planar member.

44. A method as in claim 37, wherein the vibrating step further comprises vibrating substantially all of the apertures in the non-planar member in unison.

45. A method as in claim 37, wherein the liquid is a medicament, and further comprising supplying liquid to the non-planar member such that substantially all of the delivered liquid adheres to the non-planar member by surface tension.

46. A method as in claim 37, wherein vibrating step further comprises removably attaching a vibrating source about the housing and actuating the vibrating source.

47. A method as in claim 46, further comprising removing the vibrating source and discarding the housing.

* * * * *